United States Patent [19]

Lee

[11] Patent Number: 5,830,443
[45] Date of Patent: Nov. 3, 1998

[54] EASY PEELABLE FLEXIBLE NAIL POLISH COMPOSITION

[76] Inventor: James K. Lee, 2309 Riivendell Dr., New Lenox, Ill. 60451

[21] Appl. No.: 895,201

[22] Filed: Jul. 16, 1997

[51] Int. Cl.$^6$ ................ A61K 7/00; A61K 7/04
[52] U.S. Cl. ............................. 424/61; 424/401
[58] Field of Search ....................... 424/61, 401

[56] References Cited

U.S. PATENT DOCUMENTS

| 4,126,144 | 11/1978 | Duarte | 132/73 |
| 5,120,529 | 6/1992 | Koch et al. | 424/61 |
| 5,601,808 | 2/1997 | Mellul et al. | 424/61 |

*Primary Examiner*—Thurman K. Page
*Assistant Examiner*—Sharon Howard
*Attorney, Agent, or Firm*—Sherman & Shalloway

[57] ABSTRACT

A water-based peelable nail polish is formed from a first aliphatic polyurethane having an elongation of not less than about 450%, such as 500%, and a second aliphatic polyurethane having an elongation of not more than about 250%, such as about 200%. The first and second polyurethanes are present at a mixing ratio of the first to second polyurethane in the range of from about 8:92 to about 20:80. The coatings dry in a relatively short time and remain hard and flexible and resistant to chipping, marring and fraying or sloughing for up to about 3 days or longer. The dry coatings are easily removed by simply peeling or stripping the coating from the nail without requiring any solvents or tools.

7 Claims, No Drawings

EASY PEELABLE FLEXIBLE NAIL POLISH COMPOSITION

BACKGROUND OF THE INVENTION

1. Field of Invention

This invention relates to a strippable nail polish composition which may be easily applied to and then easily peeled or stripped from human nails. More particularly, this invention relates to an aqueous based nail polish composition which can be easily applied to nails and which is sufficiently hard and flexible to be resistant to chipping but is easily peeled off the fingernail.

2. Discussion of Prior Art

Substantially all nail polishes now in the market are solvent-based, catalyzed nitrocellulose lacquer using formaldehyde resin for cross linking. Formaldehyde resin has been implicated as a carcinogen. In addition, solvents, such as toluene, n-butyl acetate and ethyl acetate may be hazardous substances: toxicity (and possibly carcinogenic) and/or low flash point (e.g., flammable).

A water-based nail polish which consists of 12 to 50 percent by weight of polyurethane and/or a polyurethane copolymer in dispersed form as a binder, 0.1 to 1 percent by weight of a thickener and water, as well as water-soluble, natural and/or synthetic resins, colorants, surfactants, drying accelerators, is the subject of U.S. Pat. No. 5,120,529. The preferred and exemplified polyurethane is a polyurethane-acrylate copolymer. No details of the polyurethane are provided nor are the films obtained from the composition noted to be peelable or to have any other specific properties.

A peelable human nail coating composition is described in U.S. Pat. No. 4,126,144 to Duarte. This composition is an aqueous latex polymer emulsion of polyvinyl resin, including polyvinyl acetate homopolymer and/or polyvinyl acetate-ethylene copolymer resin which may be stabilized by inclusion of partially acetylated polyvinyl alcohol.

U.S. Pat. No. 5,601,808 to Mellul, et al. describes certain aqueous dispersions of particles of at least one polyurethane and at least one radical-polymerization polymer containing carboxyl groups, wherein the polyurethane has a glass transition temperature (Tg) less than or equal to 30° C. The radical-polymerization polymer is typically and acrylic resin, especially an acrylic/styrene copolymer. These aqueous dispersions are used as film-forming agents in cosmetic compositions for application to a nail. The patent indicates that these compositions which satisfy certain physico-chemical criteria form a hard and glassy homogeneous film which adheres well to the nail, while being capable of being peeled off.

Nevertheless, in actual practice it has been found by the present inventor that the above types of aqueous based, peelable, formulations have certain drawbacks and do not always allow for the applied coating to be easily removed from the nail, especially from the cuticle of the nail.

For example, the compositions according to Mellul, as a result of the incorporation of the acrylic polymer tend to be hard and relatively inflexible. Such compositions are apparently designed for long wear however they are not free from chipping or marring due to the somewhat brittle nature of the coating.

Therefore, it would be highly advantageous to provide a nail coating composition which is water-based and formaldehyde-free and, therefore, presents no health concerns to the user and presents environmental hazards upon disposal. It would be especially advantageous to provide such a nail coating composition which may be easily applied to nails to form a hard, but flexible nail coating yet which is easily removed from the nails and cuticle after as short a time as about 1 to 2 hours or as long as several days. Such a nail coating composition would enable the user to select a particular color nail polish to coincide with the user's clothing, etc., for a specific event, and then to easily remove the colored film from the nail at the conclusion of the specific event; or to wear the same colored nail polish for one or a few days before removal.

It would similarly be advantageous to provide such a composition which may be formulated in a wide variety of colors using appropriate water-insoluble pigments and easily removed by peeling in just a single piece, even where the coating comes into contact with the cuticle of the finger nail.

The present invention provides nail coating compositions which meet the above objectives while still achieving the hardness and gloss similar to present nitrocellulose based nail lacquers. The coating compositions of this invention, however, may be easily removed from the fingernails by peeling it off without using any harmful, low flash point solvents commonly used for nail polish removal.

The above and other features and objectives have been accomplished with a nail polish coating composition which is an aqueous mixture of two different polyurethane dispersions, one of which is present in a minor amount and is characterized by an elongation of at least about 450% and the other of which is present in a major amount and is characterized by an elongation of no more than about 250%, and a coloring effective amount of water-insoluble pigment (s).

DETAILED DESCRIPTION AND PREFERRED EMBODIMENTS

The compositions according to the invention have the following properties:

(1) Drying time: normally as fast as or faster than solvent based formulations;

(2) Gloss and Appearance: similar to solvent based nitrocellulose formulations;

(3) Initial Hardness: able to resist marring or scuffing as soon as coating becomes dry;

(4) Extended Hardness: able to resist marring or scuffing from several hours to several (e.g., about 1 to 3) days;

(5) Flexibility: more flexible than solvent based nitrocellulose type polishes and lacquers; able to resist chipping common to hard solvent based polishes;

(6) Environmentally friendly and non-toxic;

(7) Peelability: able to be peeled easily in substantially single piece;

(8) Adhesion: good adhesion, including edges of nails, to resist fraying during normal and active wear, including, for example, while doing housework such as washing dishes and the like.

After extensive research it was found that the above properties and characteristics could be achieved by an appropriate blend of two different polyurethane film forming resins which are available as aqueous dispersions; one of the polyurethanes providing films having low elongation and being present in major proportion and contributing to the hardness, drying time, gloss and flexibility, the other of which provides films having high elongation and contributing to the peelability and adhesion of the coated films.

Accordingly, the compositions of this invention are characterized in that they comprise an aqueous dispersion of a first aliphatic polyurethane having an elongation of at least about 450% and a second aliphatic polyurethane having an elongation of not more than about 250%. The first and second polyurethanes are present in the composition, on a dry basis, at a weight ratio of from about 8:92 to about 20:80, preferably from about 10:90 to 18:82, such as about 12:88, 13:87, 15:85, 17:83.

The low elongation polyurethane is characterized by an elongation, of free films obtained from the aqueous dispersion, which is no more than about 250%, especially from about 150 to 250%, more preferably, from about 175 to 225%.

The high elongation polyurethane is characterized by an elongation, of free films obtained from the aqueous dispersion, which is at least about 450%, especially from about 450 to 600%, preferably from about 475 to 525%.

When the amount of the first or high elongation polyurethane is too high, the dry coating becomes too soft and tacky and the drying time is usually too long. Also, the dried coatings tend to mar too easily. Whereas, when the amount of the high elongation polymer is too low, the dry coating adheres too tightly to the nail, making peeling off in one piece very difficult. Additionally, without an adequate amount of the high elongation polyurethane, the coatings tend to fray when exposed to warm or hot water, such as might occur while doing housework, such as washing dishes, or even while washing hands with hot soapy water. Conversely, the amount of the low elongation polymer is chosen within the above amounts and proportions to provide adequate hardness and flexibility to the coating to resist chipping or marring of the coating. Further, within the above proportions the coating compositions dry within a relatively short time, such as about 3 to 5 minutes.

Furthermore, within the recited proportions, the coating will adhere to the nail to form a hard and glossy finish yet with sufficient flexibility so that when the coated nail is bent, such as during typing or other activity, the coating will not chip or crack. Moreover, however, within these ratios the adhesion to the nail is such that the coating may be stripped or peeled off the nail in essentially one single piece, even where the coating is applied to the skin or cuticle of the nail.

The coating compositions of this invention are aqueous formulations, essentially free of organic solvents, although small amounts of organic liquid materials may be used to achieve particular functional effects, as will be described below. The compositions will dry relatively quickly to provide a finish with high gloss in addition to the desirable hardness, flexibility and peelability.

The aqueous dispersions of the invention may be easily prepared by simply mixing the two aqueous polyurethane dispersions under slow agitation (e.g., less than about 100 r.p.m.) to avoid foaming, then adding to the mixer any additives and finally adding the pigment(s). The mixing may be carried out at room temperature and no special precautions or mixing equipment is required.

The low elongation polyurethane(s) is the major film forming component and is present in an amount, usually in the range of from about 20 to 55 percent, by weight, on a solid basis, of the total composition; preferably from about 25 to 35 percent of the total composition, such as about 28%, 29%, 30%, 31%, 32%, etc. The high elongation polyurethane(s) film-forming component is present in a minor amount, usually in the range of from about 2 to 5 percent by weight, on a solids basis, of the total composition, preferably in the range of from about 2.5 to 4 percent by weight of the total composition, more preferably, from about 2.8 to 3.8% of the total composition, such as about 3.0%, 3.2%, 3.3%, 3.4%, 3.5%, 3.6%, 3.8%, etc.

Furthermore, within these ranges of the individual polyurethane resins the proportion of the high to low elongation resins will be within the range of from about 8:92 to 20:80, especially, about 12:88 to 15:85.

Generally, therefore, the total amount of the film-forming polyurethane resin components in the coating composition will be from about 20 to 60 percent, by weight, preferably from about 25 to 50 percent by weight, especially from about 25 to 40 percent by weight, based on the total composition.

Standard additives, such as spreading agents, wetting agents, dispersing agents, thickening agents, antifoams, preservatives, UV screening agents, moisturizers, and inorganic or organic pigments, alone or mixed, may also be added to the compositions.

In particular, pigments of either inorganic or organic type are usually and preferably included in the compositions to achieve the desired color and shade. Usually, amounts of pigment in the range of from about 0.5 to about 5 percent, by weight, based on the total composition will be used. The precise amount and type or types of pigments will be selected to provide the desired color and/or shade.

One of the advantages of the nail coating compositions of this invention is that essentially the same basic film-forming ingredients and other additives, if any, may be used with a wide variety of pigment types and a wide range of colors. The ingredients of the compositions are relatively inexpensive so that it is economically feasible to purchase sets of nail coating compositions with many different colors and shades, such as for example 5 to 10 or more. This will allow the user to apply individual colors to match the clothing or occasion for which the colored coating is needed and after as few as 2 or 3 hours or after 2 or 3 days the coating may be easily removed simply by stripping or peeling the coating from the nail. No solvents or other special treatment is required.

Suitable aqueous aliphatic polyurethane dispersions are commercially available. A representative example of a low elongation aliphatic polyurethane is available from Zeneca Resins (Wilmington, Mass.) under the trade name NeoRez R-960 (34% solids). Clear films (1 mil, dry, cast on untreated cold rolled steel, after 7 days curing at ambient conditions) from this resin have a Pencil hardness of 3 H. The free films have an elongation of 200%, and 100% modulus of 4000 psi and a tensile strength of 6500 psi.

A representative example of a high elongation aliphatic polyurethane is NeoRez R-962 (Zeneca). This product also is sold as a 34%, by weight, solids dispersion. The clear films of R-962 (1.0 mil dry film, cast on cold rolled steel and force dried for 20 minutes at 200° C.) have a Pencil Hardness of 3 H. The free films have a 100% modulus of 900 psi, ultimate tensile strength of 3500 psi, and ultimate elongation of 500%.

Any other known or commercially available aqueous or waterborne dispersions of aliphatic polyurethanes may be used so long as they have an elongation within one of the specified ranges. Mixtures of two or more high elongation and/or low elongation polyurethanes may also be used.

The invention is described below by representative but non-limiting examples of specific embodiments.

Example 1

The following ingredients are blended in an agitating mixer operating at less than 100 rpm, each ingredient is added in the recited order:

| Ingredient | Amount (parts by weight) |
| --- | --- |
| NeoRez R-960 (34% solids) | 6.97 |
| NeoRez R-962 (34% solids) | 0.93 |
| Antifoaming agent | 0.03 |
| Surface Tension Modifier (Flow aid) | 0.01 |
| Butyl Cellosolve (coalescing solvent) | 0.10 |
| Water | 0.36 |
| Pigment (Deep organ red) | 0.27 |
| Pigment (white) | 0.18 |
| Pigment (black) | 0.01 |

When the above "parts by weight" represent pounds the formulation makes about 1 gallon of composition. The composition flows readily and uniformly when applied to nails and forms a glossy hard and flexible finish when allowed to dry in air. Drying is accomplished in just a few minutes, usually within five minutes or less.

For best results, the nails should be cleaned, e.g., with soap and water, before application of the coating composition. In particular, the nails should be free of hand cream or lotion residues.

Even better adhesion may be achieved by first applying a clear composition, such as described above, but without pigments. The clear coat may be applied to the entire nail, including the underside tip of the nail. It is also possible to apply multiple, usually 2, coatings of the pigmented compositions of the invention. Still additional glossiness may be obtained by, after allowing the pigmented coat or coats to thoroughly dry, applying an extra clear coat of the mixed polyurethane resin aqueous dispersion according to the invention.

Example 2

| Ingredient | Amount (parts by weight) |
| --- | --- |
| NeoRez R-960 (34% solids) | 6.90 |
| NeoRez R-962 (34% solids) | 0.92 |
| Antifoaming agent | 0.03 |
| Surface Tension Modifier (Flow aid) | 0.01 |
| Butyl Cellosolve (coalescing solvent) | 0.10 |
| Water | 0.36 |
| Pigment (Deep organ red) | 0.42 |
| Pigment (Red oxide) | 0.07 |
| Pigment (Violet) | 0.05 |
| Pigment (black) | 0.004 |

Here again, the proportions are provided for making one gallon of composition when the parts are in pounds. This composition has similar properties to the composition of Example 1.

What I claim is:

1. A nail polish coating composition comprising an aqueous dispersion of a mixture of first and second polyurethane resins, said first polyurethane resin being present in a minor amount and having an elongation of at least about 450% and said second polyurethane resin being present in a major amount and having an elongation of no more than about 250%, and a coloring effective amount of water-insoluble pigment(s).

2. The nail polish coating composition of claim 1 wherein the first polyurethane is an aliphatic polyurethane resin having an elongation of from about 450% to about 600% and the second polyurethane is an aliphatic polyurethane resin having an elongation of from about 150% to about 250%.

3. The nail polish composition of claim 2 wherein the ratio, by weight, on a solids basis, of the first polyurethane resin to second polyurethane is from about 8:92 to about 20:80.

4. The nail polish composition of claim 2 wherein the ratio, by weight, on a solids basis, of the first polyurethane resin to second polyurethane is from about 10:90 to about 18:82.

5. The nail polish composition of claim 1 containing about 20 to 60 percent by weight, on a solids basis, of the first and second polyurethane resins.

6. The nail polish composition of claim 1 which comprises an aqueous dispersion of about 25 to 28 percent, by weight, of at least one aliphatic polyurethane having an elongation of about 200%;

about 3.0 to 3.6 percent by weight, of at least one aliphatic polyurethane having an elongation of about 500%;

about 0.5 to 5 percent by weight of at least one pigment; and water.

7. A nail polish coating composition comprising an aqueous dispersion of film-forming resin and a coloring effective amount of at least one water-insoluble pigment;

said film-forming resin consisting essentially of high elongation polyurethane resin having an elongation of at least about 450% and low elongation polyurethane resin having an elongation of no more than about 250%, wherein the ration, by weight, on a solids basis, of the high elongation polyurethane to the low elongation polyurethane is from about 8:92 to about 18:82; and wherein a dried film of said coating composition on a nail may be peeled off the nail in substantially a single piece.

* * * * *